United States Patent [19]
Rosenblatt

[11] Patent Number: 5,662,594
[45] Date of Patent: Sep. 2, 1997

[54] DYNAMIC EXOSKELETAL ORTHOSIS

[76] Inventor: Marc Rosenblatt, P.O. Box 659, Monsey, N.Y. 10952

[21] Appl. No.: 489,150

[22] Filed: Jun. 9, 1995

[51] Int. Cl.$^6$ ............................................. A61F 5/00
[52] U.S. Cl. ........................ 602/16; 602/20; 602/23; 2/2.5
[58] Field of Search ................................. 128/877, 878, 128/881; 602/4, 5, 16, 19–21, 23–29; 2/2.5

[56] References Cited

U.S. PATENT DOCUMENTS

| | | | |
|---|---|---|---|
| 1,269,019 | 6/1918 | Szmyt | 2/2.5 |
| 1,269,930 | 6/1918 | Hawley | 2/2.5 |
| 1,418,283 | 6/1922 | Cameron | 602/16 |
| 3,779,654 | 12/1973 | Horne | 602/16 X |
| 4,409,689 | 10/1983 | Buring et al. | 602/16 X |
| 4,573,455 | 3/1986 | Hoy | 602/16 |
| 5,020,790 | 6/1991 | Beard et al. | 602/16 |
| 5,117,814 | 6/1992 | Luttrell et al. | |
| 5,178,137 | 1/1993 | Goor et al. | |
| 5,219,323 | 6/1993 | Singer et al. | 602/20 X |

*Primary Examiner*—Linda C. Dvorak
*Attorney, Agent, or Firm*—McHale & Slavin, P.A.

[57] ABSTRACT

The instant invention is a dynamic exoskeletal orthosis apparatus that operates as an adjustable protective brace for the protection and rehabilitation of joints. The instant invention provides protection to a joint with provisions to allow for the graduated increase in range of motion in one, two or more planes while limiting or allowing free motion in the remainder of the planes. The device allows the protection, mobilization, and stabilization of an injured joint or limb without the necessity of changing the device or utilizing multiple orthotic devices. The device is especially suitable for use in sports by providing a device that allows for a full range of movement, yet protects against impact as well as prohibits movement into positions that may lead to injury.

15 Claims, 2 Drawing Sheets

5,662,594

DYNAMIC EXOSKELETAL ORTHOSIS

FIELD OF THE INVENTION

The instant invention relates to orthotic devices and, in particular, a dynamic exoskeletal orthotic device having provisions to secure a joint or limb and provide defined mobility along any or all planes.

BACKGROUND OF THE INVENTION

It is a common belief that an injury, trauma or congenital deformation to a joint or limb must be immobilized to be corrected. For this reason the joint or limb is wrapped in a cast for months at a time to effectuate healing. For example, a brace or splint is secured to the body used to maintain alignment during a fracture healing of a bone. Immobilization of a joint or limb results in atrophy secondary due to lack of use. For example, in order to protect the elbow status-post surgical correction for ulnar entrapment immobilizers may be used. However, immobilizers lack range of motion allowing for adhesion to disuse atrophy. Improvements in this area have been mainly directed towards the use of lighter materials that improve the construction, comfort and hygiene of those individuals in need of fixation to various extremities.

Orthotics is a broad term that is used for devices that may be applied to the body to restrict or enhance motion or to simply support a body segment. The body has several types of movable joints. Ball and socket joints, which allow free movement in all directions, are found in the hip and shoulder. Hinge joints, allowing movement in one plane only, are found in the elbows, knees, and fingers. Pivot joints, permitting rotation are found between the first two vertebra. Gliding joints, in which the surface of the bones move a short distance over each other, are found between various bones of the wrist and ankle. Orthotics being a branch of biotechnology deals with the application of force through a mechanical device. Orthotic treatment may also be useful in the management of patients having various injuries to the joints including fractures of a long bone, rupture of muscles, cartilage and tendons. Some of the earlier evidence of orthotics dates back to Hippocrates who describes in detail methods of influencing the position of joints and stabilizing fractures.

Off-the-shelf orthoses can be professionally fit in a doctor's office and are typically selected by measurement of the anatomical segment. In other instances the orthoses is custom-made. In either event the function of the device is to influence body segments by the application of force to provide support, correction, or stabilization. This may provide mobility to a weakened muscle. However, it is not uncommon for the orthosis device to fail the expectations placed on it due to either spastic muscle groups, excessive reaction forces, or simply the weakening of the surrounding muscle.

Still other orthotic devices are used to protect and area. For instance, in order to protect the elbow status-post surgical correction for ulnar entrapment immobilizers may be used. Such devices afford protection but lack range of motion allowing for adhesions to disuse atrophy.

A further problem in the art is the lack of protection available to prevent injury in sporting activities. While devices exist to cushion impact, no known devices exist designed to allow a full range of motion yet prevent movement into positions that may lead to injury. For example, a race car driver requires a full range of motion but should an accident occur, the prevention of overextension may prevent breakage of the arm. This applies to basketball, football, or any other type of sport.

Further, no protection is known for otherwise non-contact sports such as equestrian or polo. For instance, equestrian riding may place a person's back in a precarious position during jumping. Commonly such riders use no protection and should they fall they could break their neck or otherwise damage there spine. Use of a pad cushion does nothing to prevent such injury.

Attempts to provide dynamic braces have been made such as U.S. Pat. No. 5,117,814 sets forth a dynamic splint that couples to the upper and lower arm but fails to provide rotation support.

U.S. Pat. No. 5,178,137 discloses a segmented dynamic splint which accommodates normal joint component motion including triplanar motion but fails to provide a stability or protection.

Thus, orthotic devices typically serve to provide either stability, mobility, or protectablity. What is lacking in the art is a device capable of performing all three functions.

SUMMARY OF THE INVENTION

The instant invention is a device that operates as an exoskeletal supporting structure for the stability, mobility and predictability of joints and limbs. The device provides dynamic exoskeletal orthosis mobility along the desired planes and locks out undesired planes. Further, the device provides stability and protection.

In one embodiment the instant invention is used to support an arm or other body joint while allowing the flexing and extending of the arm through normal joint motion including triplanar motion. The arm embodiment includes a first rigid section preferably constructed of plastic that is secured around the upper portion, humerus, of an arm and a second rigid section preferably constructed of plastic, that is secured around the lower portion, radius, of the arm. The upper portion and lower portion are coupled together by a multi-piece shell elbow joint having a common pivot point allowing pivotal movement of the shell. The shell includes various coupling points so as to secure each section in a fixed position allowing for a limited range of motion. In addition, the lower portion can be secured to the elbow section and thereby fixated in a position relative to the upper portion by use of adjustable securement screws.

In this manner, an injury may be rehabilitated by allowing movement of the arm in a predetermined noninjurious direction allowing the injured portion of the arm to heal yet providing freedom of movement so as to maintain muscle tone in circulation through the arm thereby allowing hastened recovery. A wrist section can be further attached to the lower arm portion for use in maintaining the wrist in a fixed position or allowing the wrist to be used as a support element should another part of the arm such as the radius be injured. In this manner, the wrist section operates to position or limit movement of the wrist in a particular direction.

Dr. Marc Rosenblatt, the inventor, working in close cooperation with Dr. Joseph John Rizzuto, II, an orthotics specialist, further perfected the invention through a close cooperation between medicine and engineering by focusing on the biomechanical deficits of the prior art with an initial prototype manufactured by John Bergen and Jamalm Shafiullah. In particular the invention allows for the graduated increase in range of motion in one, two or more planes while limiting or allowing free motion in the remainder of the planes while maximizing protection. As an injury heals the rehabilitation may allow for the range of motion to change wherein the device allows for altered graduation of range of motion without the necessity of changing the brace or utilizing other orthotic devices.

Unique to this invention is its ability to operate as a protective as well as corrective brace in order to prevent injuries from occurring. For instance, a symptom known as carpal tunnel syndrome has developed due to repetitive tasks particularly aggravated by improper arm positioning. In this instance, the instant invention can be used by a person and once correctly positioned will prevent the individual from improperly positioning their hands leading to the carpal tunnel injury. Thus the invention may operate as a training device prohibiting the individual from placing their wrist in an improper position thereby providing a positive reinforcement as to the correct positioning for the particular task. A result is that after a period of time the individual will be trained in the proper placement of the wrist for the task. For example, typists and prolific computer keyboard operators are notorious for improper positioning of their arms when performing such a repetitive task as that demanded by a keyboard where an individual maintains their fingers in an exact location. In this instance, the device would be used to train the individual in proper placement of their arms and wrists as the device will absolutely prohibit movement into the improper position.

Injury prevention can further be directed into sports. For instance, numerous sports utilize elbow pads to protect the funny bone which is the medial epicondyle of the humerus. The funny bone gaining its terminology because pressure applied over this area stimulates the ulnar nerve and produces a distinct sensation. While an elbow pad provides cushioning to this area, it does not protect the area nor prevent improper movement of the elbows. Hockey is such a sport that propels an individual at a high speed and should the individual fall or be clipped it is probable that their arm may be twisted in such a position so as to cause temporary if not permanent injury.

Temporary injury may be as simplistic as bruising the funny bone or as serious as breaking a long bone. Permanent injury may be a result of over extending a muscle causing a torn ligament. The instant invention allows for attachment to a healthy arm. In other embodiments a finger, knee, ankle, spine, foot and so forth may use the teachings of the instant invention so as to protect the joint from injuries yet provide a device that prevents improper joint movement which can lead to permanent injury.

Thus, an objective of the instant invention is to teach a dynamic exoskeletal orthosis device which can be easily attached to a limb or joint providing protection, mobility and stability. The device having a full range of motion is allowed at any and all planes with full protection being maintained. The device may be anchored distally via the radius or more proximally if necessary.

Yet another objective of the instant invention is to disclose a brace having dynamic capabilities allowing pre-described movements of areas surrounding an injured area providing enhanced rehabilitation to the particular area by providing continuing movement of joints surrounding the affected area to maintain muscle tone hastening rehabilitation.

Still another objective of the instant invention is to provide a brace that operates as a training device for use in situations where improper joint movement can lead to injury. As an example, prevention of carpal tunnel syndrome.

Yet still another objective of the instant invention is to set forth a device for protection of an arm to prevent improper extension of a healthy arm which may lead to injury.

Still another objective of the instant invention is provide a protective device that mimics a joint in movement.

Yet still another objective of the instant invention is to disclose a shell mechanism with adjustment screws that can be used on any limb or joint of the human body as well as disclose a device adaptable to animals such as horses and dogs.

Other objectives and advantages of this invention will become apparent from the following description taken in conjunction with the accompanying drawings wherein are set forth by way of illustration and example, certain embodiments of this invention. The drawings constitute a part of the specification and include exemplary embodiments of the present invention and illustrate various objects and features thereof.

DETAILED DESCRIPTION OF THE PREFERRED EMBODIMENT

Although the invention has been described in terms of a specific embodiment, it will be readily apparent to those skilled in this art that various modifications, rearrangements and substitutions can be made without departing from the spirit of the invention. The scope of the invention is defined by the claims appended hereto. In light of the various types of joints that may be based upon the instant invention, it is believed that it would be most appropriate to set forth a specific embodiment directed to the protection of the arm as the elbow sets forth a hinge joint and a wrist uses a gliding joint.

Figure 1:
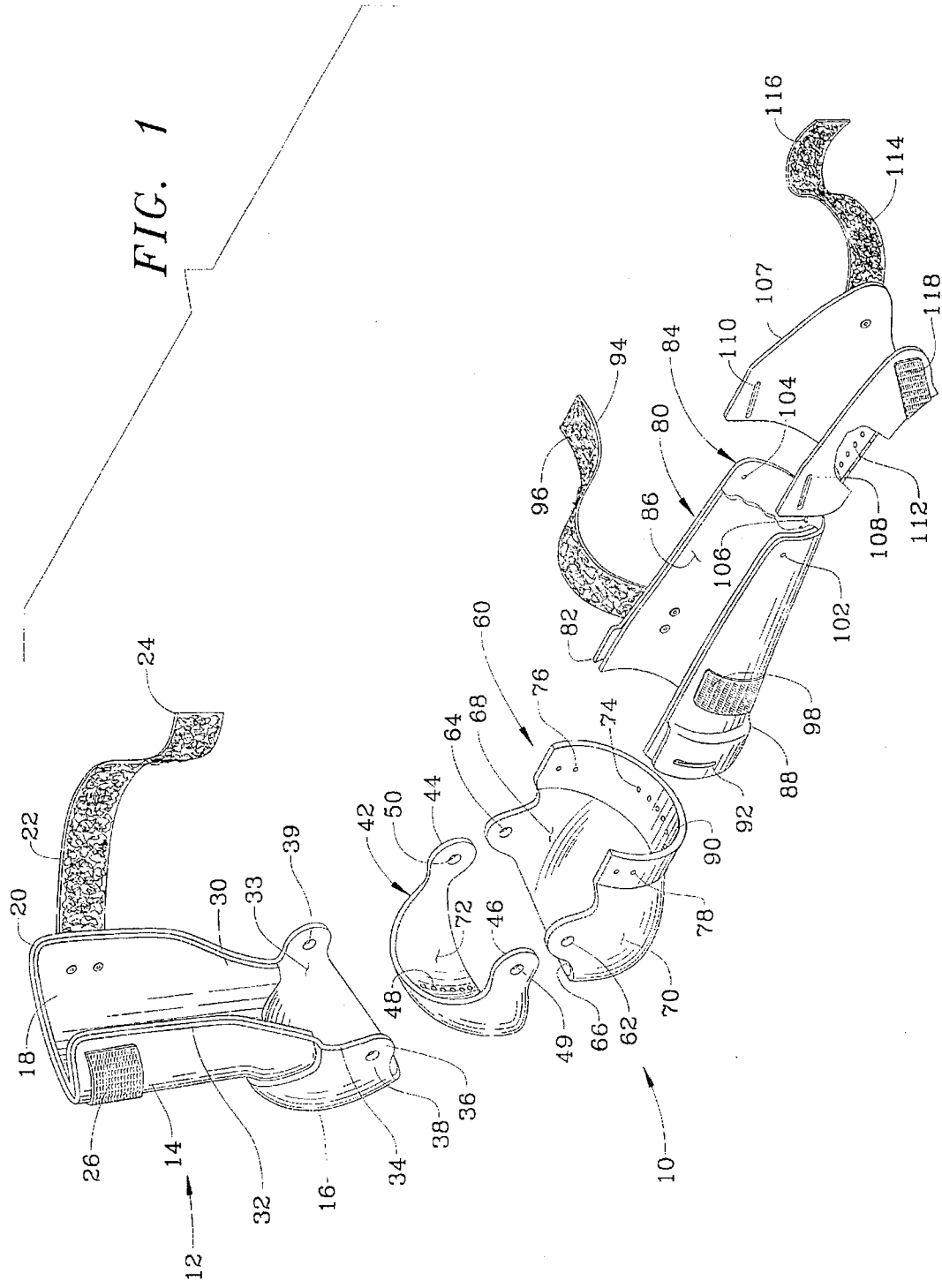
FIG. 1 is an exploded perspective view of the instant invention.
Figure 2:
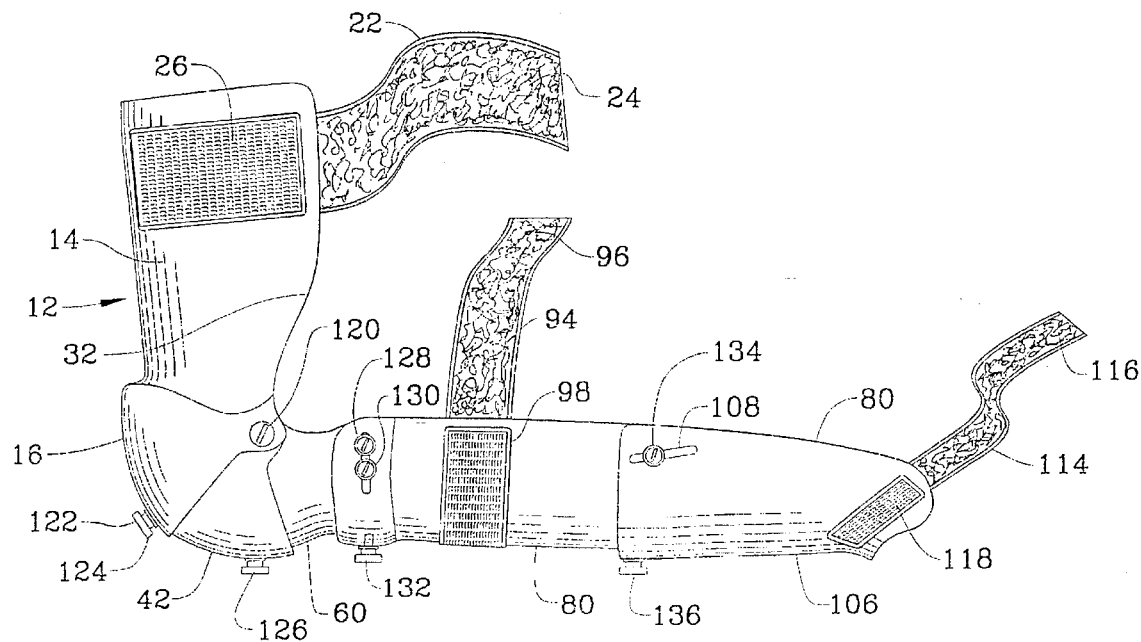
FIG. 2 is a plane side view of the instant invention.
Figure 3:
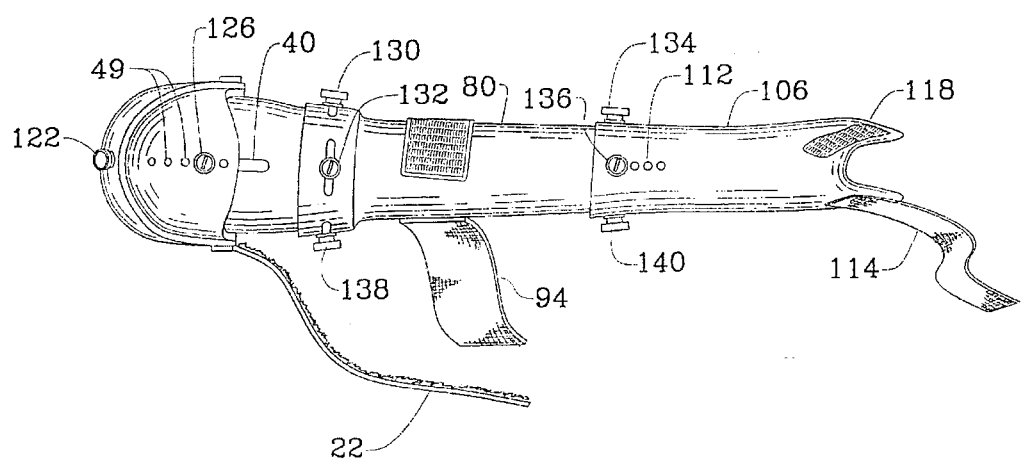
FIG. 3 is a plane bottom view of the instant invention.

Now referring in general to FIGS. 1-3, set forth is an embodiment of the dynamic exoskeletal orthosis device according to the teachings of the instant invention directed to the bracing of a human arm. In this embodiment the device 10 provides a controlled movement through a programmable range of motion.

The device 10 consists of a first member 12 which is secured to the upper arm of an individual relying upon the support of the humerus. As will be described later in this invention, if the humerus is damaged, the device will supply support thereto. The upper member 12 consists of an upper section defined by a rigid shell 14 having length with a substantially U-shaped curvature allowing for placement against the backside or triceps muscle of an arm. A lower section 16 of the first member 12 is enlarged defining a curvature encompassing a portion of said rigid shell and formed integral thereto. The lower section 16 is shaped to accommodate and protect the individual's elbow, namely, the lateral and medial epicondyle. A cushioning pad 18 is positioned along an inner surface 20 of the rigid shell 14 providing a cushion to the arm and a moisture barrier layer.

Flexible strap 22 is secured to a side surface of the shell 14 for use in wrapping around the front of the arm with free end 24 available for securement to an opposite end 26 of the strap secured to an outer surface of the shell 14, ends 24 and 26 having a receptacle hook and loop VELCRO type attachment. It is noted the rigid shell 14 is enlarged along each side edge forming the U-shaped section to accommodate the triceps of a person which is typically larger than the brachialis muscle. For this reason, a lower portion 30 of the shell 14 is slightly narrowed with a frontal edge 32 forming a curvature backward to the leading edge of the upper elbow shell edge 34. The elbow shell edge 34 forming a hinge joint 36 having apertures 38 and 39 to be used in coupling multiple articulating shells as will be described later in this specification. Aperture 39 is positioned across from the first aperture 38 creating an axis of movement between the two apertures. The lower portion 16 of the shell 14 has an inner surface 33 which is formed toward the rear of the shell including sufficient room sideward area to encompass the lateral and medial epicondynale of humerus. The lower portion 16 of the shell includes an adjustment slot 40.

In the upper arm there is but one bone, the humerus. The upper part of the bone is at first cylindrical and as it approaches the elbow it flattens out and expands sideways. There are two joint surfaces, side-by-side, at the expanded end of the humerus. The inner one resembles a spool, pulley or hour glass laid on its side and is known as the trochlea. The part of the ulna that bends around the trochlea of the humerus is commonly referred to as the "funny bone". The nerve running to the ulna passes close by it and when we strike the bone this nerve tingles. The lower portion 16 the aforementioned second and third members provide an ancillary benefit of protecting the funny bone.

The second member 42 is operatively associated with the upper member 12 by use of coupling ends 44 and 46 having mounting aperture 50 and 48 respectively, allowing for alignment and the pivotal rotation along said axis of movement with apertures 38 and 39 of the first member. The second member 42 is defined by a curved shell which is slidably insertable along an outer curvature of the lower portion 16 of the first member 12. A plurality of through hole mounting holes 49 are centrally disposed and positionable over adjustment slot 40 and available for the threadable insertion of an adjustable locking screw for maintaining the upper member 12 in a fixed position relative to the second member 42 and further for allowing for an angular rotation along the axis of movement formed by mounting apertures 48 and 50 which may be further locked in position by use of the locking screws 122 having an enlarged head 124 for ease of rotation by human fingers. The inner surface 72 is formed backward toward the rear of the shell including sufficient sideward room pursuant to the upper member 12 to encompass the lateral and medial epicondynale. Locking screws may simply have an enlarged head 124 allowing for ease of rotation of an embedded screw or another type of locking means may be utilized such as a push and release type screw mechanism wherein the upper member has provisions for being locked in position in relation to the second member by depression of a locking screw fixating the components together. The screws described through this specification may be color coded providing ease of instruction and operation of which locking mechanism that needs to be moved in order to position a component in proper relation to a second member or in relation to the entire brace. It is further noted that the invention is not limited by locking by use of said screws as it is well known that various locking mechanisms may be used such as friction pins, spring loaded tabs, wedges, and so forth, all of which are embodied by this invention as a means for limiting the movement of the members.

Third member 60 is operatively associated with the second member 42 using coupling apertures 62 and 64 for engaging apertures 48 and 50 of the second member 42, and 38 and 39 of the upper member 12. The third member 60 employs an elongated slot 66 which allows for the securable positioning of the second member 42, or a range of motion, by placement of a threaded screw attachment 126 or the like which fits through the slot 66 and is securable to one of the mounting apertures 49 of the second member 42. The inner surface 68 of the member allows placement of the elbow with the outer surface 70 sized to allow for the slidable insertion along inner surface 72 of the second member 42. An insertion sleeve portion 90 is formed along one end of the member having three sections of adjustment hole 74, 76 and 78 positioned about the insertion sleeve.

The inner bone of the forearm, the ulna, hooks onto the trochlea form behind. Because the ulna is primarily concerned with bending and straightening the elbow, it is thick and massive at the elbow and tappers at the wrist. The radius carries the hand at the wrist and so is thick and heavy there and narrows at the elbow to the same type or kind of disc like head that the unit displays at the wrist. The radius of the arm is protected by lower member 80 which is also formed from a rigid elongated shell having a first end 82 and a second end 84 with a padded surface liner 86 along an inner side surface of the shell. First end 82 is enlarged using a step ridge 88 extending outwardly from the liner 86 for attachment to the insertion sleeve 90 of the third member 60. The sleeve 90 with adjustment slot 92 is placed through the shell for attachment to mounting aperture holes 76, 78 and 74. As with the upper member, the lower member includes a flexible strap 94 having a hook and loop attachment 96 on one end of the strap available for wrapping around the arm of an individual placed within the shell with the strap releasably securing to receptive end 98 thereby relying upon the radius bone in a fixed position or if necessary providing limited movement to the radius and ulna as allowed by adjustment to the device. Adjustment screw 132 is placed through the slot located on the lower member. Similarly each side of the shell is secured by side attachment screws 130 and 138 each allowing for adjustment of the lower member in respect to the radius. Along second end 84 is a first wrist mounting aperture 102, second mounting aperture 104 and adjustment slot 106.

Wrist member 107 is formed from a one piece rigid shell having adjustment slot 108 operatively associated with mounting aperture 102, upper adjustment slot 110 is operatively associated with second mounting aperture 104. Adjustment slot 106 of the lower member 80 is positionable between locking aperture holes 112 located along a bottom of the wrist member 107 allowing adjustment of wrist movement thereof. As with the upper member 12 and lower member 80, strap 114 is provided for placement between the thumb and first finger so as to maintain the carpal bones and metacarpal bones in a fixed position if necessary. The strap 114 includes a hook and loop attachment 116 available for placement to a receiving hook and loop attachment 118 thereby fixating the wrist in a pre-determined position. When the palm of the hand is directed forward and then the thumb is pointing away from the body, the radius and ulna lie side-by-side. As the palm is turned, wherein the thumb is directed toward the body the radius turns and the lower end rolls across the ulna. A frontal section of the elbow member is substantially U-shaped with centrally disposed mounting apertures 74 and securement holes 76 and 78 located along an upper end of the centrally mounted holes.

It is to be understood that while I have illustrated and described certain forms of my invention, it is not to be limited to the specific forms or arrangement of parts herein described and shown. It will be apparent to those skilled in the art that various changes may be made without departing from the scope of the invention and the invention is not to be considered limited to what is shown in the drawings and described in the specification. The teachings of the invention may easily be directed to stability and mobility of the femur and fibula providing protection to the patella.

What is claimed is:

1. A dynamic exoskeletal orthosis apparatus comprising: an upper member constructed from a single piece of rigid material securable to a limb adjacent a joint; a first and second junctional member each constructed from a single piece of rigid material, said first junctional member pivotally coupled to said upper member allowing pivotal movement of said upper member and said first junctional member in the form of a hinge joint; means for limiting said pivotal movement; a lower member constructed from a single piece of rigid material rotationally coupled to said second junctional member allowing rotational movement of said lower member along a longitudinal axis in relation to said second junctional member; a means for limiting said rotational movement; said first and second junctional members hingably connected to allow pivotal movement therebetween; and a means for securing said upper member and lower member to the limb.

2. The apparatus according to claim 1 wherein said means for securing said upper member and said lower member to the limb is further defined as a flexible strap having a base end secured to an outer surface of each said member having free end having a hook and loop material engagable to said base end, said strap adjustable to accommodate limb size.

3. A dynamic exoskeletal orthosis apparatus comprising: an upper member constructed from a single piece of rigid material of nominal thickness having a proximal end, a first intermediate end, and opposing side edges defining an inner surface and an outer surface, said proximal end forming a U-shaped support for placement about a limb, said first intermediate end forming an enlarged semi-circular joint with said opposing side edges having a corresponding pivot point;

means for securing said upper member to the limb; a first junctional member constructed from a single piece of rigid material of nominal thickness having a second intermediate end, an insertion end, and opposing side edges defining an inner surface and an outer surface with said side edges having a corresponding pivot point operatively associated with said pivot point of said intermediate end allowing rotation of said first junctional member in relation to said upper member along a common axis formed by said pivot point, said outer surface of said second intermediate end slidable along said inner surface of said first intermediate end of said upper member; means for limiting the pivotal movement of said upper member and said first junctional member; a second junctional member constructed from a single piece of rigid material pivotally coupled to said upper member and said first junctional member along said pivot points, said second junctional member having a means for limiting movement of said upper member and said first junctional member; a lower member constructed from a single piece of rigid material of nominal thickness having a receptacle end, a distal end, and opposing side edges defining an inner surface and an outer surface, said distal end forming a U-shaped support for placement about a limb, said receptacle end operatively associated with said second junctional member providing longitudinal rotation therebetween; means for securing said lower member to the limb; and a means for limiting the rotation movement of said junction member and said lower member.

4. The apparatus according to claim 3 wherein said means for securing said upper member and said lower member to the limb is further defined as a flexible strap having a base end secured to said outer surface of each said member having free end having a hook and loop material engagable to said base end, said strap adjustable to accommodate limb size.

5. The apparatus according to claim 3 wherein said means for limiting said pivotal and rotational movement is defined as a plurality of coupling holes formed in one of said members with an overlaying slot formed in an adjacent member, said coupling holes receptive to at least one locking screw limiting movement of each member relative to the positioning of said locking screw to said length of said slot.

6. The apparatus according to claim 5 wherein said locking screws are color coded.

7. The apparatus according to claim 3 including a cushioning pad secured to an inner surface of said upper member and said lower member.

8. The apparatus according to claim 3 including a plastic wrist member, said wrist member having a first end adjustably securable along a longitudinal length and angular slope to said lower member and a second end securable to a hand.

9. The apparatus according to claim 8 including a cushioning pad secured to an inner surface of said wrist member.

10. The orthosis apparatus according to claim 3 wherein said members are constructed of plastic.

11. A dynamic exoskeletal orthosis apparatus comprising:

an upper member constructed from a single piece of rigid plastic material of nominal thickness having a proximal end, a first intermediate end, and opposing side edges defining an inner surface and an outer surface, said proximal end forming a U-shaped support for placement about a limb, said first intermediate end forming an enlarged semi-circular joint with said opposing side edges having a corresponding pivot point;

a first flexible strap having a base end secured to said outer surface of said upper member having free end engagable with said base end, said strap adjustable to accommodate limb size;

a first junctional member constructed from a single piece of rigid plastic material of nominal thickness having a second intermediate end, an insertion end, and opposing side edges defining an inner surface and an outer surface with said side edges having a corresponding pivot point operative associated with said pivot point of said first member allowing rotation of said first junctional member in relation to said upper member along a common axis formed by said pivot point, said outer surface of said second intermediate end slidable along said inner surface of said first intermediate end of said upper member having a means for limiting the pivotal movement of said upper member and said junction member;

a second junctional member constructed from a single piece of rigid plastic material pivotal coupled to said upper member and said first junctional member along said pivot points, said second junctional member having a means for limiting movement of said upper member and said first junctional member;

a lower member constructed from a single piece of rigid plastic material of nominal thickness having a receptacle end, a distal end, and opposing side edges defining an inner surface and an outer surface, said distal end forming a U-shaped support for placement about a limb, said receptacle end operatively associated with said insertion end providing longitudinal rotation therebetween;

a second flexible strap having a base end secured to said outer surface of said lower member having free end engagable with said base end, said strap adjustable to accommodate limb size;

and a means for limiting the rotation movement of said junction member and said lower member.

12. The orthosis apparatus according to claim 11 wherein said means for limiting is defined as a plurality of coupling holes formed in an encompassed member with an overlaying slot having a length in an associated member, said coupling holes receptive to at least one locking screw limiting movement of each member relative to the positioning of said locking screw to said length of said slot.

13. The orthosis apparatus according to claim 11 including a cushioning pad secured to said inner surface of said upper member and said lower member.

14. The orthosis apparatus according to claim 11 including a wrist member, said wrist member having a first end adjustably securable along a longitudinal length and angular slope to said lower member and a second end securable to a hand.

15. The apparatus according to claim 14 wherein said wrist member is positionable to support the hand, said wrist member having an inner surface receptive to the metacarpal bones and securable to the hand by means of a strap positionable between the thumb and index finger.

* * * * *